United States Patent [19]

Nitsch et al.

[11] Patent Number: 4,629,698

[45] Date of Patent: Dec. 16, 1986

[54] PLASMA EXPANDER BASED ON STARCH

[75] Inventors: Ernst Nitsch, Linz; Hubert P. Ferber, Ansfelden; Siegfried Mühlböck, Linz, all of Austria

[73] Assignee: Laevosan-Gesellschaft mbH & Co. KG Chemisch-Pharmazeutische Industrie, Linz, Austria

[21] Appl. No.: 690,674

[22] Filed: Jan. 11, 1985

[51] Int. Cl.$^4$ .................. C12P 19/14; C12P 19/22; C12P 19/16

[52] U.S. Cl. .................................. 435/95; 435/98; 435/99

[58] Field of Search .................. 424/101; 435/95, 98, 435/99, 101, 103; 127/36, 38; 514/833

[56] References Cited

U.S. PATENT DOCUMENTS 2,571,541 10/1951 Cleland et al. .................. 127/36
3,523,938 8/1970 Hershenson et al. .................. 127/36
3,927,204 12/1975 Neri et al. .................. 424/101

OTHER PUBLICATIONS

Whistler et al., 1965, Starch Chemistry and Technology, vol. 1, Academic Press, New York, pp. 155–157, 160–163, 168–169, 375–377, 497–501.

Primary Examiner—Raymond N. Jones
Assistant Examiner—Carolyn Paden
Attorney, Agent, or Firm—Felfe & Lynch

[57] ABSTRACT

The present invention provides a process for the preparation of a plasma based on starch by the hydrolytic decomposition of an amylopectin-rich starch to a definite molecular weight and partial etherification to a definite substitution before or after the hydrolysis, wherein the hydrolytic decomposition is carried out at least partly with α-amylase, β-amylase or pullulanase.

14 Claims, 1 Drawing Figure

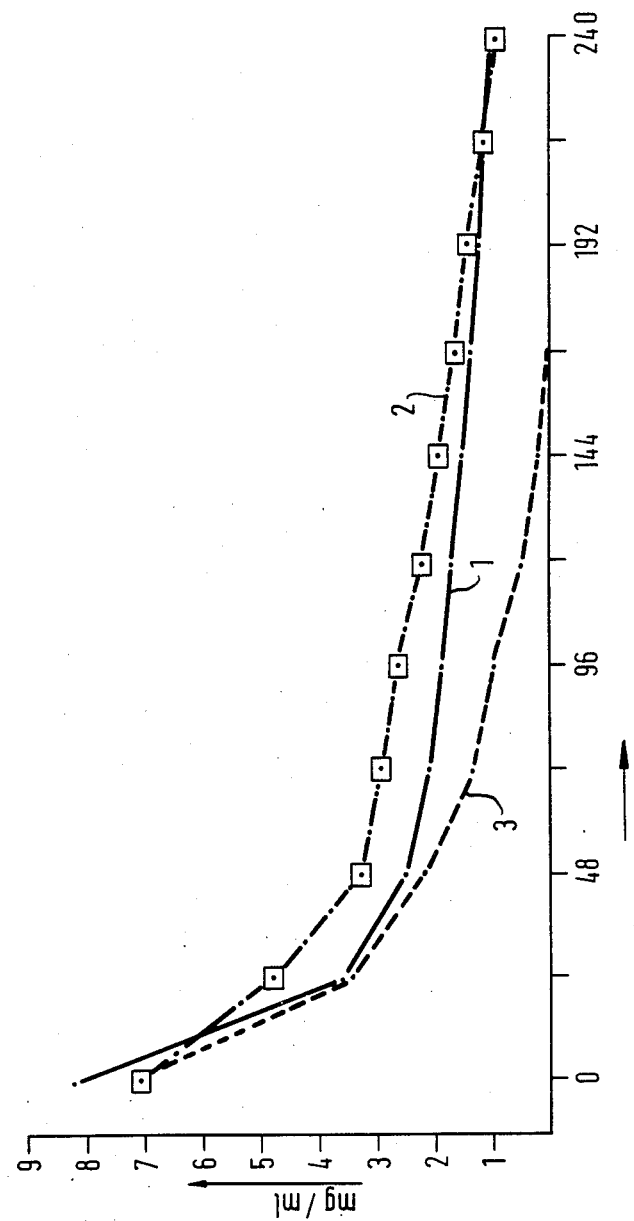

PLASMA EXPANDER BASED ON STARCH

The present invention is concerned with a plasma expander based on starch and with a process for the preparation thereof.

There is an ever-increasing need for blood plasma volume agents (plasma expander). For a good suitability, plasma expander should display a concentration drop within the first 24 hours which is as steep as possible and should also have an organ half-life time which is as short as possible. There prerequisites are satisfied by dextran. However, a disadvantage of the use of dextran is the possibility of the appearance of allergic reactions.

U.S. Pat. No. 3,523,938 and Federal Republic of Germany Patent Specification No. 2,837,067 describe plasma expander based on partly etherified starch, for example hydroxyethyl starch. These products are obtained by hydrolysing a starch with a high amylopectin content to a viscosity range corresponding to a definite molecular weight range by means of an acid, followed by an alkaline etherification with, for example, ethylene oxide. The sequence of the steps of hydrolytic decomposition and etherification can be reversed. The plasma expander obtained according to this process possess, in comparison with dextran, the advantage that no allergic reactions appear but they have the disadvantage of a substantially slower breakdown.

Therefore, it is an object of the present invention to provide a plasma expander which does not display these disadvantages and which, on the basis of its properties, is very well suited as a plasma expander.

Thus, according to the present invention, there is provided a process for the preparation of a plasma expander based on starch by the hydrolytic decomposition of an amylopectin-rich starch to a definite molecular weight and partial etherification to a definite molar substitution before or after the hydrolysis, wherein the hydrolytic decomposition is carried out at least partly with $\alpha$-amylase, $\beta$-amylase or pullulanase.

Surprisingly, we have found that, by means of the process according to the present invention, plasma expander are obtained which do not give rise to any allergic reactions and, in comparison with the previously known, partial etherified starches, for example hydroxyethyl-starch (HES), are characterised by a steep concentration drop within the first 24 hours and by a short organ half-life time.

Preferred plasma expander prepared according to the present invention include hydroxyethyl-starch 450/07 (450,000 Dalton, molar substitution 0.7) and hydroxyethyl-starch 200/05 (200,000 Dalton, molar substitution 0.5).

As starch starting material, there is used an amylopectin-rich starch such as is also used, for example, as starting material for the processes according to U.S. Pat. No. 3,523,938 and for Federal Republic of Germany Patent Specification No. 2,837,067. Such as starch is, for example, a waxy starch, such as waxy milo (sorghum) starch, waxy maize starch or waxy rice starch. Such waxy starches consist mainly of amylopectin and have a low amylose content. Waxy starches which are used in the process according to the present invention preferably contain 90% by weight or more of amylopectin. Gelatinized starches can also be used but the starch is, however, preferably gelatinised immediately before or simultaneously with the hydrolysis.

According to the process of the present invention, the starch decomposition is carried out at least partly by enzymatic means, i.e. the starch decomposition consists of a combination of an acid decomposition step and of an enzymatic decomposition step or, preferably, only of an enzymatic decomposition step. The enzymatic decomposition is carried out by means of pullulanase and especially by means of $\alpha$- or $\beta$-amylase. Of the amylases, $\alpha$-amylase is preferably used, especially when using a combination of acid decomposition and enzyme decomposition. As $\alpha$-amylase, there is preferably used a thermally stable $\alpha$-amylase preparation, for example an $\alpha$-amylase obtainable from thermophilic bacteria.

The reaction conditions correspond to the conditions conventionally employed in the case of enzymatic hydrolyses. In general, the concentration of the starch in the aqueous suspension is about 20 to 50% by weight and especially from 30 to 40% by weight, referred to the dry weight of the starch. In the case of the use of a thermally stable $\alpha$-amylase preparation, the period of time of the decomposition step can thereby be considerably shortened because it is possible to work at comparatively high reaction temperatures, for example of from 70° to 95° C. $\alpha$-Amylases of other origin, which must be used at lower temperatures, for example at a temperature of from 20° to 50° C., can also be used but with a correspondingly longer reaction time. In general, the reaction time, which is especially dependent upon the desired degree of hydrolysis and upon the reaction temperature or upon the amylase used, is from 0.5 to 10 hours. An especial advantage in the case of the use of thermally stable $\alpha$-amylase preparations is also the fact that gelatinisation (glutinisation) and decomposition take place in parallel, i.e. in one step, whereas in the case of lower temperatures, the gelatinisation must, under certain circumstances, take place previously in a separate step.

The hydrolytic decomposition can be carried out before or after the etherification. However, in general, it is preferred to carry it out before the etherification. An etherification following the hydrolytic decomposition can be followed by a further enzymatic decomposition step.

The etherification takes place under per se known conditions, such as are described, for example, in U.S. Pat. No. 3,523,938 and in Federal Republic of Germany Patent Specification No. 2,837,067, by treating the starch with an alkylene oxide or alkylene chlorhydrin in the presence of an alkali. The degree of substitution is preferably controlled by varying the amount of alkylene oxide used. In this case, it is necessary to use an amount in excess of that calculated to be required for the desired molar substitution because the corresponding glycol is also partly formed. There are preferably prepared the hydroxypropyl and especially the hydroxyethyl ethers by reaction with propylene oxide and ethylene oxide, respectively.

For the removal of glycol, salts and other low molecular weight contaminations, the hydrolysed and etherified product is subjected to a purification operation.

For this purpose, the process product obtained after hydrolysis/etherification is preferably subjected to a subsequent diafiltration. In this way, the initial concentration in the serum (measured in mg./ml.), which is to be as high as possible, can be improved. In the case of the dialysis, besides salts and other low molecular weight substances, there can also be removed low molecular weight decomposition products of <40,000

Dalton. Although use can be made of a dialysis membrane with a molecular weight exclusion limit of from 10,000 to 100,000 Dalton, it is preferable to use a membrane with a molecular weight exclusion limit of 40,000 Dalton and especially of 50,000 Dalton. In this way, there is obtained a high molecular weight, uniform product which permits a high initial concentration.

The product can be converted into a dry powder by methods known for this purpose, for example spray drying, drum drying or vacuum drying. This powder, as well as the product obtained after the purification and especially after the diafiltration, can be stored and, when required, can be converted into blood plasma substitutes suitable for infusion in the usual manner by dissolving in a physiological salt solution or plasma salt solution usual for infusion purposes. The concentration of the hydroxyalkyl-starches according to the present invention in these plasma expander is generally from 4 to 10% by weight and especially of about 6% by weight.

The hydrolytic decomposition is preferably carried out to a molecular weight range of from 40,000 to 1,000,000 Dalton and especially of from 200,000 to 450,000 Dalton.

The etherification is carried out up to a molar substitution range (number of hydroxyalkyl ether groups per anhydroglucose unit of the starch) of from 0.1 to 0.8 and especially of from 0.5 to 0.7.

The degree of hydrolysis determines the viscosity (limiting viscosity number, intrinsic viscosity) of the end product. Therefore, the degree of hydrolysis and the end of the hydrolysis can be ascertained by determination of the viscosity during the hydrolysis.

The following Examples are given for the purpose of illustrating the present invention:

EXAMPLE 1

Hydroxyethyl-starch HES 450/07 with an average molecular weight of about 450,000 Dalton and a molar substitution of 0.7 mole hydroxyethyl ether groups/mole of anhydroglucose.

In a heatable kettle, an amount of waxy maize starch corresponding to a dry weight of 25 kg. was suspended in 59 kg. of distilled water with the help of a vigorous stirrer, 40 g. calcium chloride hexahydrate and 3 ml. Termamyl 60 L (thermostable α-amylase; obtained from Novo, Bagsvaerd, Denmark) were added thereto and the mixture was rapidly heated to about 95° C. After passing through the gelatinisation stage, there was formed a viscous but readily stirrable solution. After 2 hours at the same temperature, the relative viscosity of a 20% by weight solution at 20° C. had decreased to $n_{rel}=2.10$. The enzyme was inactivated by the addition of 25 ml. concentrated hydrochloric acid (pH of the solution of 3.0) and the turbid solution of the decomposed amylopectin, after stirring in 1.25 kg. active powdered charcoal, was filtered through filter layers of Zeta Plus 1 Dep (obtained from Cuno, European Division, Wiesbaden, Germany). The clear, colourless, slightly opalescent filtrate contained, after subsequent washing, 23.0 kg. of decomposed amylopectin (AS) and 84.5 kg. of water. It was etherified in a gas-tight reaction kettle with 3.38 kg. (=0.6 mole/mole AS) sodium hydroxide and 6.06 kg. (=0.97 mole/mole AS) ethylene oxide for 2 hours at 20° to 25° C. Subsequently, the pH value was adjusted with hydrochloric acid to pH 5.0 and the solution was subjected to a diafiltration, with the volume being kept constant with distilled water, with the help of two hollow fibre modules BMR 504515 (obtained from Berghof, Tübingen; exclusion limit 50,000 Dalton) until the chloride content in the filtrate had decreased to below 10 ppm, referred to the dry weight of the retentate.

The retentate was filtered through filter layers of Zeta Plus 1 Dep, the clear yellow-coloured solution obtained was dried in a vacuum drying cabinet at 60° C. and the material obtained was then ground.

The molar substitution (MS) was 0.72 mole of hydroxyethyl ether groups/mole of anhydroglucose and the limiting viscosity number /n/ was 29.7 ml./g. The yield was 10.0 kg.

EXAMPLE 2

Hydroxyethyl-starch HES 200/05 with an average molecular weight of about 200,000 Dalton and a molar substitution of 0.5 mole hydroxyethyl ether groups/mole of anhydroglucose.

The batch for the enzymatic hydrolysis was carried out as in Example 1 but hydrolysis was carried out for 3 hours to a relative viscosity of $n_{rel}=1.45$. The filtrate contained 20.0 kg. of decomposed amylopectin and 80.5 kg. of water. Etherification took place with 2.96 kg. (=0.6 mole/mole AS) sodium hydroxide and 3.80 kg. (=0.7 mole/mole AS) ethylene oxide.

In the case of otherwise the same manner of operating as in Example 1, there were obtained 9.0 kg. hydroxyethyl-starch MS=0.53; /n/=19.4 ml./g.

EXAMPLE 3

Hydroxyethyl-starch HES 40/05 with an average molecular weight of about 40,000 Dalton and a molar substitution of 0.5 mole hydroxyethyl ether groups/mole of anhydroglucose.

Batch as in Example 1, hydrolysis time 4.5 hours to $n_{rel}=1.10$. The filtrate contained 21.3 kg. of decomposed amylopectin and 81.7 kg. of water. The etherification took place with 3.15 kg. (=0.6 mole/mole AS) sodium hydroxide and 3.75 kg. (=0.65 mole/mole AS) ethylene oxide. The diafiltration took place with the use of two hollow fibre modules HF 26.5-43-PM10 (obtained from Romicon, Woburn, Mass., USA; exclusion limit 10,000 Dalton) but otherwise as described in Example 1. Yield: 8.25 kg., MS=0.45; /n/=11.07 ml./g.

Determination of the relative viscosity:

A 100 ml. volumetric pipette with a height difference between the graduation mark and the tip of 400 mm. and with a narrowing in the run-off so that the run-off time for water at 20° C. was about 75 seconds, was placed precisely vertically in a support, filled up to the mark with the solution to be measured tempered to 20° C. and the run-off time t determined precisely in seconds to 0.1 with a stopwatch. The relative viscosity $n_{rel}=t/to$ to=run-off time for water.

For the determination of the rate of breakdown of the plasma expander according to the present invention, 6.6 ml./hour HES 450/07 (6%) were administered within an infusion time of 3 hours to male Sprague-Dawley rats (number of experimental animals: 160; weight of the experimental animals: 250 to 320 kg.). The experimental animals were bled after a period of time of 24 hours up to the 230th day after the infusion and their organs were then removed. The concentration of the HES 450/07 in the serum was 15±2.36 mg./ml. on the first day and then decreased up to the 9th day by 96.14% to 0.58±0.07 mg./ml.

For the liver, according to this method, there was ascertained for the HES 450/07 according to the present invention a half-life time of 30 days, whereas the half-life time for a starch decomposed by acid hydrolysis was 132 days (cf. W. L. Thomson et al., Surg. Gynec. Obstet., 131, 965-972/1970).

In FIG. 1 of the accompanying drawings, there is compared the breakdown rate in a human experiment of (1) HES 450/07 according to the present invention, (2) commercially available HES 450/07 obtained by acid hydrolysis and (3) commercially available dextran 60. The experiments were carried out in each case on groups of 10 healthy subjects. The solutions used were all 6% and thus identical with regard to the kinetic values.

Although with (1) there is obtained a higher average serum level, the serum decrease in the first 48 hours is more rapid and more uniform than with (2) and comparable with (3) (dextran).

Similarly good results are obtained with an HES 200/05 according to the present invention.

These experiments show that the plasma expander according to the present invention display, with regard to initial concentration, concentration decrease in the first 24 hours and half-life time, more favourable properties than comparable, known plasma expander obtained by acid hydrolysis and, in the case of these properties, are comparable with those of dextran.

We claim:

1. In a process for the preparation of a starch-based plasma expander by a combination of hydrolytic decomposition of an amylopectin-rich starch to a definite molecular weight and partial etherification to a definite molar substitution, said etherification being accomplished either before or after said hydrolysis, the improvement wherein said hydrolytic decomposition comprises hydrolysis with alpha-amylase, beta-amylase or pullulanase to a molecular weight of 40,000 to 1,000,000 Dalton and said etherification being carried out to a molar substitution of from 0.1 to 0.8.

2. The process of claim 1, wherein said decomposition is carried out to a molecular weight of from 200,000 to 450,000 Dalton.

3. The process of claim 1, wherein said etherification is carried out to give an hydroxyethyl or hydroxypropyl ether.

4. The process of claim 1, wherein waxy maize starch, rice starch or milo starch is used as starch.

5. The process of claim 1, wherein said hydrolytic decomposition is carried out with alpha-amylase.

6. The process of claim 5, wherein said alpha-amylase is a thermally stable alpha-amylase preparation.

7. The process of claim 1 wherein said hydrolytic decomposition is carried out before said etherification.

8. The process of claim 1, wherein for said hydrolytic decomposition, an acid decomposition is combined with an enzymatic decomposition with alpha-amylase.

9. The process of claim 1, wherein said hydrolytic decomposition is only carried out enzymatically.

10. The process of claim 1, wherein said plasma expander is a hydroxyethyl-starch 450/07 (450,000 Dalton, degree of substitution 0.7).

11. The process of claim 1 wherein said plasma expander is a hydroxyethyl-starch 200/05 (200,000 Dalton, degree of substitution 0.5).

12. The process of claim 1 further comprising, after said hydrolytic decomposition and a subsequent etherification, a second enzymatic decomposition step.

13. The process of claim 1 further comprising after said hydrolytic decomposition and etherification, subjecting the product to diafiltration.

14. The process of claim 13, wherein a dialysis membrane is used with a molecular weight exclusion limit of from 10,000 to 100,000 Dalton.

* * * * *